US012616850B2

(12) United States Patent
Liu et al.

(10) Patent No.: US 12,616,850 B2
(45) Date of Patent: May 5, 2026

(54) VIRTUAL PARTICLE BASED MONTE CARLO DOSE CALCULATION FOR CHARGED PARTICLE THERAPY TREATMENT PLANNING

(71) Applicant: Mayo Foundation for Medical Education and Research, Rochester, MN (US)

(72) Inventors: Wei Liu, Scottsdale, AZ (US); Jie Shan, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 892 days.

(21) Appl. No.: 17/832,122

(22) Filed: Jun. 3, 2022

(65) Prior Publication Data

US 2023/0390579 A1 Dec. 7, 2023

(51) Int. Cl.
*A61N 5/10* (2006.01)

(52) U.S. Cl.
CPC ........... *A61N 5/103* (2013.01); *A61N 5/1031* (2013.01); *A61N 5/1048* (2013.01); *A61N 2005/1034* (2013.01); *A61N 2005/1087* (2013.01); *A61N 2005/1089* (2013.01)

(58) Field of Classification Search
CPC .... A61N 5/103; A61N 5/1031; A61N 5/1048; A61N 2005/1034
See application file for complete search history.

(56) References Cited

U.S. PATENT DOCUMENTS

| | | | |
|---|---|---|---|
| 6,285,969 B1 * | 9/2001 | Svatos | A61N 5/1031 |
| | | | 703/2 |
| 7,650,265 B2 | 1/2010 | Taylor et al. | |
| 7,756,693 B2 | 7/2010 | Shima et al. | |
| 8,125,813 B2 | 2/2012 | Nizin et al. | |
| 8,680,487 B2 | 3/2014 | Nishio et al. | |

(Continued)

FOREIGN PATENT DOCUMENTS

| | | |
|---|---|---|
| CN | 104318330 A | 1/2015 |
| CN | 104484535 A | 4/2015 |

(Continued)

OTHER PUBLICATIONS

Chamberland, M. et al., egs_brachy: A Versatile and Fast Monte Carlo Code for Brachytherapy, Physics in Medicine & Biology, 2016, 61:8214-8231.

(Continued)

*Primary Examiner* — Brian W Wathen
(74) *Attorney, Agent, or Firm* — Quarles & Brady LLP

(57) ABSTRACT

Radiation treatment planning for charged particle therapy systems, such as proton therapy systems, includes calculating dose distribution(s) using a virtual particle Monte Carlo ("VPMC") dose calculation engine that utilizes virtual particles. Virtual particles inherit the physical properties from realistic particles, but are conceptually designed for parallel computing in graphics processing units ("GPUs") by avoiding the simulation of secondary particles. Simulation of virtual particles instead of realistic particles takes full advantage of the GPU hardware architecture (e.g., by avoiding thread divergence and racing conditions).

18 Claims, 5 Drawing Sheets

(56) References Cited

U.S. PATENT DOCUMENTS

| | | | |
|---|---|---|---|
| 2002/0106054 A1* | 8/2002 | Caflisch | A61N 5/1031 |
| | | | 378/65 |
| 2010/0054536 A1 | 3/2010 | Huang et al. | |
| 2013/0329982 A1 | 12/2013 | Alghamdi et al. | |
| 2015/0352374 A1* | 12/2015 | Gattiker | A61N 5/1031 |
| | | | 703/2 |
| 2016/0328253 A1 | 11/2016 | Majumdar | |
| 2020/0054276 A1 | 2/2020 | Chakravarty et al. | |
| 2020/0206539 A1 | 7/2020 | Han et al. | |

FOREIGN PATENT DOCUMENTS

| | | |
|---|---|---|
| CN | 106355017 A | 1/2017 |
| CN | 108197355 A | 6/2018 |
| CN | 111539151 A | 8/2020 |
| EP | 2578270 A1 | 4/2013 |
| EP | 3400876 A1 | 11/2018 |
| JP | H11295472 A | 10/1999 |
| JP | 2006204457 A | 8/2006 |
| WO | 2012066351 A2 | 5/2012 |
| WO | 2020168257 A1 | 8/2020 |
| WO | 2022032591 A1 | 2/2022 |
| WO | 2022047637 A1 | 3/2022 |

OTHER PUBLICATIONS

Jia, X. et al., GPU-Based Fast Monte Carlo Simulation for Radiotherapy Dose Calculation, Physics in Medicine & Biology, 2011, 56(22):7017, 18 pages.

Neph, R., Accelerating Radiation Dose Calculation with High Performance Computing and Machine Learning for Large-Scale Radiotherapy Treatment Planning, University of California, Dissertation, 2020, 156 pages.

Townson, R. et al., GPU-Based Monte Carlo Radiotherapy Dose Calculation Using Phase-Space Sources, Physics in Medicine & Biology, 2013, 58(12):4341, 20 pages.

Wang, Y., Fast Monte Carlo Simulations for Quality Assurance in Radiation Therapy, Washington University Arts & Sciences Electronic Theses and Dissertations, 2017, 1205, 135 pages.

* cited by examiner

VIRTUAL PARTICLE BASED MONTE CARLO DOSE CALCULATION FOR CHARGED PARTICLE THERAPY TREATMENT PLANNING

BACKGROUND

Monte Carlo ("MC") simulations are considered as gold standards for dose calculation in radiation therapy. However, the general purpose MC codes (e.g. Geant4, MCNPX, FLUKA, and TOPAS), although accurate, are slow (e.g., taking several hours or days for one plan dose calculation) and thus unsuitable for clinical use.

Fast MC codes (e.g., gMC, gPMC, FRED, and MCsquare) are dedicated to proton dose calculations with simplified physics models and/or with the help of graphic processing unit ("GPU") acceleration. They significantly reduce the time for one plan dose calculation to several minutes. Unfortunately, these aforementioned MC codes are not yet fast enough for some advanced optimizations in spot scanning proton therapy ("SSPT") treatment planning, for example, real-time on-the-bed adaptive proton therapy (ART), 4D robust optimization and linear-energy-transfer ("LET")-guided robust optimization. In 4D robust optimization and linear-energy-transfer ("LET")-guided robust optimization, tens of scenarios need to be considered, and for each scenario hundreds of iterations of dose calculations are needed. For real-time on-the-bed ART, the dose calculation time is very sensitive since patients are lying on the treatment bed. Thus, reducing the MC calculation time to seconds or sub-seconds is required for clinical implementation of the MC dose calculation engine for real-time treatment planning and advanced optimizations.

Current fast MC codes use physics models to handle the interactions between particles and mediums. The generated secondary particles are stored in shared memory buffers. MC simulation must decide the chance, type, and momentum of the generation of various kinds of secondary particles and access the shared memory buffer at each MC step. This requires sophisticated logic controls and large shared memory buffers. Both can be handled well by central processing units ("CPUs"). However, unlike CPUs, the control logic and shared memory buffer for a single thread is very limited in GPUs. Within a block of threads, the threads are executed in groups of 32 called a warp. Thread divergence occurs when different threads in a warp need to execute different tasks. In the worst-case scenario, if one thread in a warp diverges, the 32 threads in this warp might need to stop and revert to the end of the previous step to redo the dose calculation. Therefore, GPUs might lose a factor of 32 in the computing performance. Thread divergence is a significant problem in GPU-based proton dose calculation engines if the "one particle per thread" technique (a GPU thread tracks a particle until the end conditions are satisfied) is adopted in the design of parallelization.

Racing condition is another significant problem in large-scale shared memory parallel computation, where multiple threads happen to access and manipulate the same shared memory address simultaneously, resulting in possible memory conflicts among different threads. The generation of secondary particles is random and leads to sophisticated computation logic and unexpected computation burdens to the corresponding thread. The randomly increased number of particles per thread due to the generation of secondary particles greatly increases the chance of racing condition.

These two problems (thread divergence and racing condition) are inherent to the hardware architecture of GPUs and prevent taking full advantage of the GPU computing power to achieve MC-based sub-second plan dose calculation based on GPUs. A real-time MC dose calculation engine that takes full advantage of the computing capabilities of GPUs is, therefore, still needed in SSPT treatment planning.

SUMMARY OF THE DISCLOSURE

The present disclosure addresses the aforementioned drawbacks by providing a treatment planning system for use with a charged particle therapy system. The treatment planning system includes a memory and a graphics processing unit ("GPU"). The memory has stored thereon a pre-calculated continuous-slowing-down-approximation ("CSDA") model that includes probability distribution functions ("PDFs") of physics parameters associated with soft particle interactions of virtual particles, a pre-calculated ionization model that includes PDFs of physics parameters associated with ionization of virtual particles, and a pre-calculated large angle scattering event ("LAE") model including PDFs of physics parameters associated with hard particle interactions of virtual particles. The GPU is configured to load the CSDA model, the ionization model, and the LAE model into a shared memory of the GPU, and to simulate virtual particles using the CSDA model, the ionization model, and the LAE model, where the virtual particles are simulated by simulating both primary charged particles and secondary particles as virtual particles that start at the same starting location of a primary charged particle. The GPU is also configured to calculate a dose distribution of the primary charged particles and the secondary particles based on the simulated virtual particles.

It is another aspect of the present disclosure to provide a method for generating treatment plan data for use with a charged particle therapy system. The method includes loading, to a shared memory of a GPU: a pre-calculated CSDA model that includes PDFs of physics parameters associated with soft particle interactions of virtual particles, a pre-calculated ionization model that includes PDFs of physics parameters associated with ionization of virtual particles, and a pre-calculated LAE model that includes PDFs of physics parameters associated with hard particle interactions of virtual particles. Virtual particles are simulated using the GPU, where simulating the virtual particles includes simulating both primary charged particles and secondary particles as virtual particles that start at the same starting location of a primary charged particle. The virtual particles are simulated by assigning each virtual particle to a thread of the GPU, thereby minimizing thread divergence and racing conditions in the GPU, and in each of a plurality of steps: calculating a phase space for each virtual particle based on at least one of the CSDA model, the ionization model, or the LAE model, and updating each virtual particle based on its calculated phase space. Dose distribution data are generated based on dose scoring the simulated virtual particles using a computer system, which may be the GPU or a separate computer system. The dose distribution data are stored as part of treatment plan data for use with a charged particle therapy system.

The foregoing and other aspects and advantages of the present disclosure will appear from the following description. In the description, reference is made to the accompanying drawings that form a part hereof, and in which there is shown by way of illustration one or more embodiments. These embodiments do not necessarily represent the full scope of the invention, however, and reference is therefore made to the claims and herein for interpreting the scope of the invention.

DETAILED DESCRIPTION

Figure 1A:
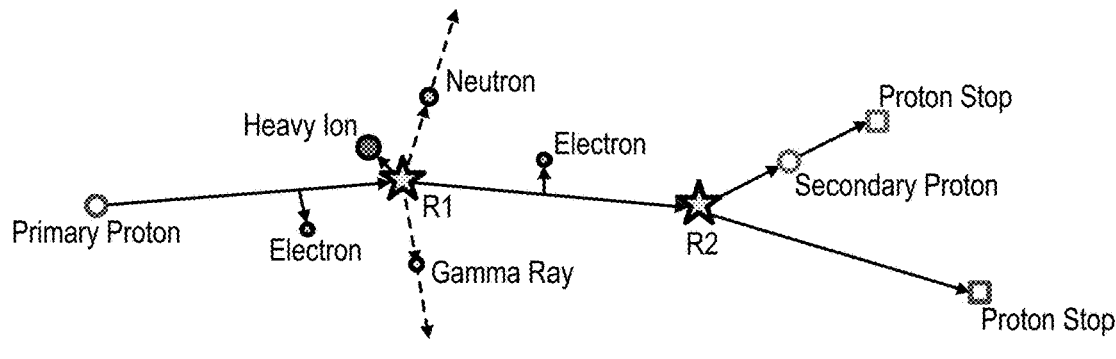
FIGS. 1A-1D illustrate the conversion of primary proton and secondary particle track histories to virtual particles.

Described here are systems and methods for radiation treatment planning for charged particle therapy systems, such as proton therapy systems. In particular, the radiation treatment planning include generating a charged particle dose distribution us a Monte Carlo ("MC")-based dose calculation engine that utilizes virtual particles. As will be described below in more detail, virtual particles inherit relevant physical properties from realistic particles, but are conceptually designed for parallel computing in graphics processing units ("GPUs") by avoiding the simulation of secondary particles. Simulation of virtual particles instead of realistic particles (e.g., primary protons and secondary particles) can take full advantage of the unique hardware architectures of GPUs (i.e., many simultaneous threads, but simple control logics and limited shared memory buffers for a single thread), leading to greatly enhanced usage efficiency of the computing power of GPUs and sub-second plan dose calculation. Advantageously, the VPMC dose calculation engine described in the present disclosure can calculate proton dose distributions efficiently and accurately in pencil beam scanning ("PBS") applications.

As another advantage, the virtual particle Monte Carlo ("VPMC") dose calculation engine described in the present disclosure can minimize, or otherwise eliminate, thread divergence and data race conditions in the GPU(s) used to generate the dose distribution data. The dose of one primary proton and its secondaries, named realistic particles, can be recalculated by simulating multiple virtual particles. Each virtual particle corresponds to one realistic particle; however, virtual particles start at the same starting position of the primary proton. After converting the track histories of realistic particles into track histories of virtual particles that generate the same dose as realistic particles, probability models can be generated to describe the behaviors of virtual particles. Such models can be derived by performing a statistical analyses of the track histories of protons and secondary particles from a conventional MC simulation. Doses can then be calculated by simulating only virtual particles, which avoids simulating secondary particles. This enables further simplification of the models and avoids thread divergence and data race conditions in conventional MC simulations.

As will be described below in more detail, to simplify the dose calculation the VPMC dose calculation engine ignores neutrons and gamma rays as escaping from the human body; locally deposits doses of electrons, heavy ions, and nuclear fragments; and converts the tracks of deuterons into tracks of protons due to the similar behaviors shared between protons and deuterons in various materials. Histories of primary and secondary protons are replaced by histories of multiple virtual particles. Each virtual particle corresponded to one proton (either primary or secondary); however, virtual particles are started at the same starting position of the primary proton. A continuous-slowing-down-approximation ("CSDA") model, an ionization model, and a large angle scattering event ("LAE") model corresponding to nuclear interactions are developed and implemented for the virtual particles. Probability distribution functions ("PDFs") describing the CSDA, ionization, and LAE models are derived based on the track histories of virtual particles from a run of several million (e.g., 20 million) monoenergetic primary protons with infinitesimal spot sizes normally irradiating into phantoms using a conventional MC code, such as MCsquare. These PDFs can be fine-tuned in such a way that virtual particles generate dose distributions that closely match physical dose distributions. For efficient calculations, the PDFs can be stored in the Compute Unified Device Architecture ("CUDA") textures of a GPU. The phase space can be defined at the exit of the nozzle (but before any beam modifiers such as range shifters) and a double Gaussian lateral profile model can be used to model the beam source more accurately. The phase space of a particle refers to the particle's energy, momentum, and position(s).

Figure 1B:
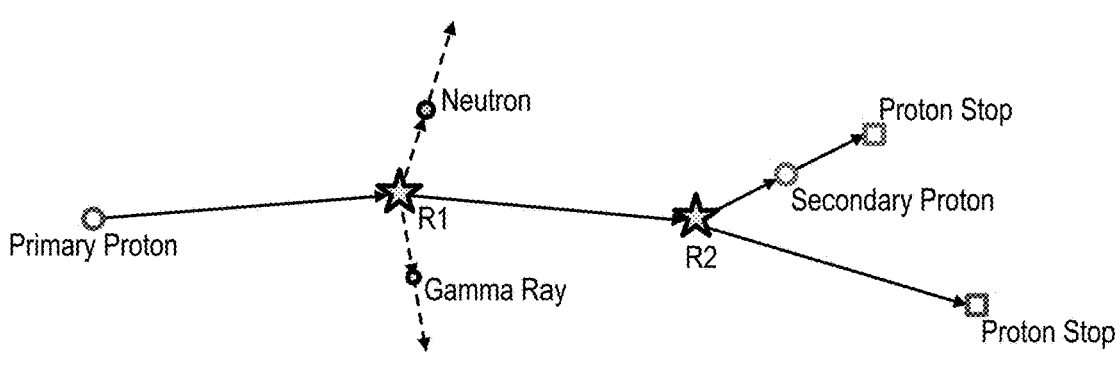
Figure 1C:
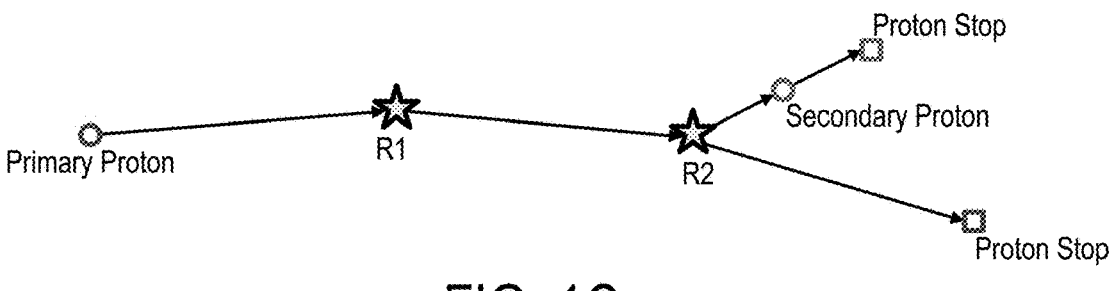
Figure 1D:
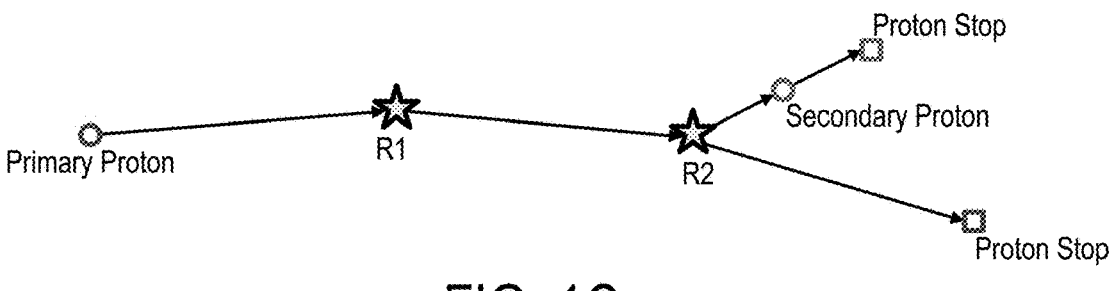

FIGS. 1A-1D illustrates an example of converting the track histories of a realistic proton and its secondaries in a conventional Monte Carlo simulation into two virtual particles. In general, FIG. 1A shows the track history of an example realistic proton. FIG. 1B shows the track history after the doses of electrons, heavy ions, and nuclear fragments have been locally deposited. FIG. 1C shows the track history after neutrons and gamma rays have been considered to escape from the subject and thus ignored. FIG. 1D then shows the track history after converting the realistic particles (e.g., one primary proton and one secondary proton) to two virtual particles that have the same path from the starting point to R2. These two virtual particles are independent from each other.

In more detail now, FIGS. 1A-1D show the process of converting the histories of realistic particles into equivalent histories of virtual particles. As noted above, three simplifications can be made to further speed up the calculations without significantly sacrificing precision: (1) the doses of electrons, heavy ions, and nuclear fragments can be locally deposited (e.g., from FIG. 1A to FIG. 1B), (2) neutrons and gamma rays can be considered to escape from the subject's body and thus ignored as energy loss, (e.g., from FIG. 1B to FIG. 1C), and (3) the tracks of deuterons can be converted into tracks of protons since their behaviors in different materials are similar. After these simplifications, one primary proton can be represented by multiple virtual particles that start at the same starting position of the primary proton (e.g., from FIG. 1C to FIG. 1D). Assuming that the number of secondary protons and deuterons generated from one primary proton in the MC simulation is M, the number of virtual particles starting at the same starting position of the primary proton would be M+1 for this primary proton. Each virtual particle can be independent from each another. Two virtual particles are shown in FIG. 1D for illustrative purposes. In FIG. 1D, virtual particle "A" and virtual particle "B" do not necessarily share the same paths before R2 and can proceed in different paths in actual MC simulations.

After converting the histories of realistic particles into histories of virtual particles that generate the same dose as realistic particles, statistical models that include PDFs of the corresponding parameters can be obtained to describe the behaviors of the virtual particles. As one non-limiting example, the models can be derived by performing a statistical analysis of the track histories of realistic protons and their corresponding secondary particles from a conventional MC simulation. In one non-limiting example, the PDFs used in the VPMC dose calculation engine can be formed based on data generated by MCsquare with 20 million primary monoenergetic protons with infinitesimal spot sizes irradiating normally into phantoms. The same materials defined during the commissioning of MCsquare for a given charged particle therapy system can be used for virtual particle model building and in the actual VPMC dose calculation in patient geometries.

A CSDA model (e.g., a condensed class-II CSDA model) can be used to describe the soft particle interactions of virtual particles. In general, soft particle interactions can include those interactions with low momentum transfer, such as angular deflections in a large number of soft collisions sampled from a continuous distribution. As an example, the soft interactions may be soft electromagnetic interactions and in some instances may be referred to as multiple Coulomb scattering ("MCS"). Rather than an on-the-fly calculation of the related physics parameters (e.g., the deposited energy, $E_{deposited}$; energy straggling $E_{straggling}$; the deflection angle, $\theta$; and the ionization probability, $P_{ion}$) based on physics models in MCsquare (and other MC codes), the VPMC described in the present disclosure directly calculates physics parameters. As a non-limiting example, for each MC step, calculations can be significantly sped up by directly calculating physics parameters using a 2D CUDA textures look up tables ("LUTs"), with two-dimension self-variables as the energy of virtual particles ("E") and the Hounsfield units ("HU") value of the virtual particle location.

To generate such CUDA textures, the energy and HU value can be scaled (e.g., 0 to 230 MeV for energy and –1050 to 29000 for HU values, respectively) in MCsquare or another suitable MC code, and the calculated physics parameters can be recorded and used to obtain PDFs describing the relationship between physics parameters and the energy and HU values, X(E, HU), where X( . . . ) a physics parameter, such as the deposited energy, energy straggling, the deflection angle, or the ionization probability. When X(E, HU) is not linear, further tuning work can be done to render VPMC to achieve higher dose accuracy.

Based on the ionization cross section interpolated from the CUDA texture generated in the CSDA step, the ionization for virtual particles can be modeled in VPMC. If ionization happens, the status of the virtual particles is updated, As one example, the status of the virtual particles can be updated based on an analytical formula similar to the one used in MCsquare or other MC dose calculation codes.

An LAE model is used to account for nuclear reactions and/or interactions. For instance, the LAE model can be used to describe hard particle interactions of virtual particles. In general, hard particle interactions can include those interactions resulting in a large momentum component that is perpendicular to the beam path (e.g., the virtual particle path). During the nuclear reactions, possible secondary particles are generated, which can result in an increased number of realistic particles. In conventional MC simulations, these secondary particles would randomly appear in the middle of the calculation (e.g., as shown in FIG. IA) and need to be tracked thereafter as primary particles, which can potentially cause thread divergence and increase the chance of racing condition in GPU threads.

In VPMC, these realistic particles (including both primary and secondary particles) are replaced by virtual particles, which appear from the very beginning of the MC simulation (e.g., as shown in FIG. 1D). Therefore, the total number of virtual particles can be predetermined before the MC simulation and the number of virtual particles can remain constant during the MC simulation.

In addition to conventional physics parameters of the nuclear reaction probability, the deposited energy, the energy loss (e.g., energies from neutrons and gamma rays escaped from human bodies), and the deflection angle, the VPMC includes another parameter referred to as "weight gain". Weight gain is the fraction of the dose contributed by one certain virtual particle at a certain step, which is used in the final dose scoring stage to get the final dose distribution, as described below in more detail. For instance, the weight gain accounts for how many times the same path is shared by multiple virtual particles. This weight gain parameter is unique to virtual particles and does not exist in the MC simulation of realistic particles.

During the dose scoring stage of the MC simulation, the weight gain can be multiplied to the dose contribution of the corresponding virtual particle within the corresponding step to get the correct dose distribution as would be generated by realistic particles. Taking FIG. 1D as an example, the first two steps of the MC simulation before the bifurcation at R2 were shared by two virtual particles; thus, these two virtual particles in these two steps could be assigned a weight gain of 0.5 for the dose scoring. Thus, in general, for M+1 virtual particles, the weight gain applied to the dose contribution of each virtual particle before bifurcation can be w=1/(M+1). In alternative implementations, other values of weight gain could be used, such as a positive real number less than or equal to one (e.g., w∈[0,1]). While after the bifurcation at R2, both virtual particles in FIG. 1D (e.g., A and B) exclusively possessed their own third step, therefore, the weight gain can be changed to 1.0 for both virtual particles for the corresponding third step during the dose scoring stage.

Similar to the CSDA model, the LAE model can be derived using the related parameters (e.g., the nuclear reaction probability, the deposited energy, the energy loss, the deflected angle, and the weight gain) that are obtained based on a pre-calculated database using MCsquare (or another suitable MC code) rather than being calculated on-the-fly. As a non-limiting example, the pre-calculated data can be generated with 20 million monoenergetic primary protons with infinitesimal spot sizes irradiating normally into phantoms stored in the a shared memory of the GPU, such as being stored in shared memories as CUDA textures for efficient calculation.

In some implementations, one or more range shifters can be modeled for inclusion in the VPMC. For example, two institution-specific range shifters can be modeled, including a range shifter positioned at the exit of nozzle (labeled as RS) and an extended range shifter positioned at an extended position (labeled as ERS). In one example implementations, the range shifters were modeled as being made of ABS resin composed of hydrogen, carbon, nitrogen, and oxygen. The water equivalent thickness in this example was 4.5 cm for both range shifters. RS was positioned at 42.5 cm from isocenter, while ERS was positioned 30 cm from isocenter. Similar to the track histories of virtual particles in patient geometries, the track histories of virtual particles in each range shifter can also be modeled by various PDFs. Because the range shifter is a generally homogenous medium with a fixed HU value (unlike the highly heterogenous patient geometries), the 2D CUDA textures for the CSDA model in patient geometries can be reduced to 1D CUDA textures with the fixed HU value corresponding to the range shifter material.

Figure 2:
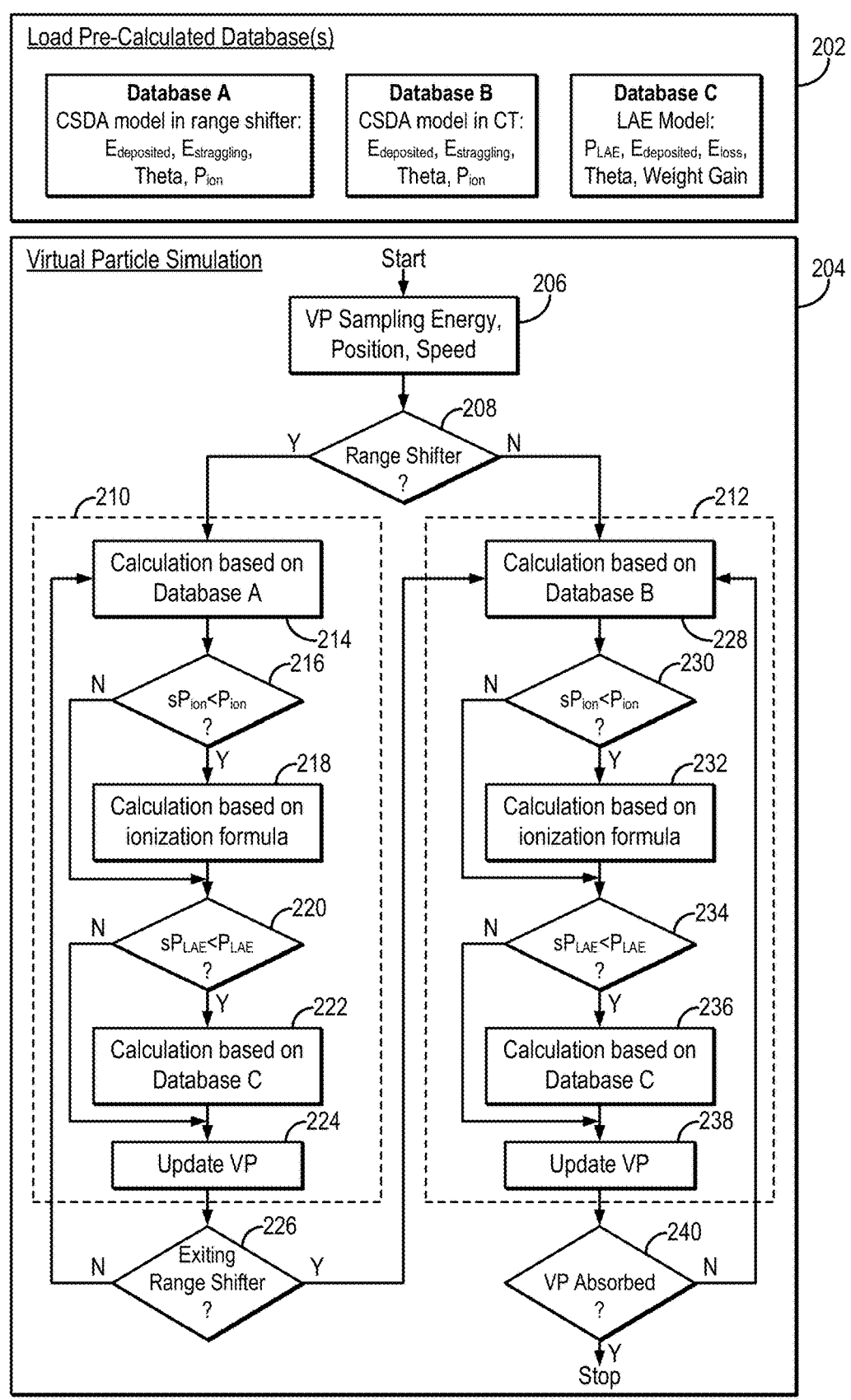
FIG. 2 illustrates an example workflow for implementing a virtual particle Monte Carlo ("VPMC") dose calculation engine.

Referring now to FIG. 2, an example workflow for a VPMC dose calculation engine is shown. In general, the VPMC dose calculation engine includes simulating virtual particle that can be interpreted based on the track histories from a conventional MC code, as described above. The dose of one primary proton (or other charged particle) and its secondaries, named realistic particles, can be regarded as if it is deposited by multiple virtual particles that start at the same starting position of the primary proton. The VPMC dose calculation engine induces one or more probability models to describe the behaviors of these virtual particles. For instance, the probability model(s) can include one or more CSDA models corresponding to soft interactions for virtual particles, one or more ionization models, and one or more LAE models corresponding to hard interactions for virtual particles. To simplify the dose calculation, in some implementations, neutrons and gamma rays can be ignored; the dose of electrons, heavy ions, and nuclear fragments can be locally deposited; and the tracks of deuterons can be converted into tracks of protons, as described above with respect to FIGS. 1A-1D.

In general, a Monte Carlo particle transport algorithm can be defined as a repetition of the following steps. A domain of possible inputs (e.g., physics parameters) is defined and inputs are randomly generated from a probability distribution over the domain. For instance, within the context of charged particle transport, the domain of inputs can correspond to the physics parameters of particle interactions, and the CSDA, ionization, and LAE models described in the present disclosure can include the probability distributions over that domain. A deterministic computation is then performed on the inputs. For instance, particle interactions and step lengths can be computed based on statistical sampling and constraints. The particles—here, the virtual particles— are then moved based on the computed information.

The dose distribution from realistic particles can then be calculated by simulating only the virtual particles in the VPMC dose calculation engine, as is now described in more detail.

In an initialization stage, pre-calculated databases of parameters, models, and/or data to be utilized by the VPMC dose calculation engine are accessed by a computer system, as indicated at process block 202. In general, the computer system includes at least one GPU, which can implement VPMC-based dose calculations. The pre-calculated databases can include one or more CSDA model databases, one or more ionization model databases, one or more LAE model databases, and so on. For example, the pre-calculated databases can include a first CSDA model database containing CSDA model data corresponding to one or more range shifters, which may include energy deposit data, energy straggling data, deflection angle data, and/or ionization probability data. Additionally or alternatively, the pre-calculated databases can include a second CSDA model database containing CSDA model data corresponding to patient geometry, which may include energy deposit data, energy straggling data, deflection angle data, and/or ionization probability data. The pre-calculated databases can also include one or more LAE model databases containing LAE model data, which can include energy deposit data, energy loss data, deflection angle data, weight gain data, and/or nuclear reaction probability data. As described above, these data can include PDFs of the respective parameters.

Once accessed or otherwise loaded, the data stored in the pre-calculated databases can be stored in the local storage of a GPU. For instance, the data loaded from the pre-calculated databases can be stored in one or more shared memories of the GPU. As described above, in some implementations the data loaded from the pre-calculated databases can be stored in shared memories as CUDA textures, which can allow for repeated and efficient access from subsequent virtual particle simulations.

For the virtual particle simulations (indicated generally as process block 204), a number of virtual particles are sampled at first with parameters of energy, position, and momentum and each virtual particle is assigned to a certain GPU thread, as indicated at step 206. In one example implementation, particle sampling can be implemented using a single set of phase space parameters suitable for each charged particle therapy system and/or charged particle therapy system configuration for which dose calculations are being performed. For instance, particle sampling can be implemented using a single set of phase space parameters for three system configurations: one without a range shifter, one with an RS range shifter, and one with an ERS range shifter.

In order to speed up the dose calculations, simulation of particle transport in the nozzle can be omitted in some implementations. In those instances, the phase space at the exit of the nozzle (but before any beam modifiers, such as range shifters) can be otherwise derived or estimated. As one non-limiting example, the phase space at the exit of the nozzle can be estimated using integrated depth dose ("IDD") curves and in-air lateral profiles at five positions of proton beams. The phase space can have a large emittance due to the scattering of the beamline components in the nozzle; thus, to model the beam source more accurately a lateral profile such as a double Gaussian lateral profile, or the like, can be used.

For a synchrotron-based system, a number of discrete energies can be commissioned (e.g., 90, 95, 100, etc. discrete energies), rather than a selected number of energies as are typical for a cyclotron-based system. The proton number per monitor unit ("MU") calibration curve and the corresponding CT calibration curve can also be commissioned accordingly as in MCsquare or other suitable MC codes.

A decision is made at decision block 208 whether one or more range shifters should be accounted for in the dose calculations. If so, then the virtual particle simulation process proceeds to the range shifter simulation process block 210. If no range shifters will be used, then the virtual particle simulation process can proceed to the patient geometry simulation process block 212.

Thus, if a range shifter (either RS or ERS) is being used, virtual particles are first simulated in the range shifter (range shifter simulation block 210) and then simulation in the patient geometry (patient geometry process block 212).

A calculation based on the CSDA model data corresponding to the range shifter is first performed at step 214. In the range shifter, by comparing the ionization probability ($P_{ion}$) calculated based on the virtual particle physics parameters and the sampled ionization probability ($sP_{ion}$) at decision block 216, the ionization process can be considered based on an analytical formula (e.g., similar to analytical formulae used in MCsquare or other suitable MC codes) when $sP_{ion}$ is less than $P_{ion}$, as indicated at step 218. As a non-limiting example, the phase space of the virtual particle can be updated based on the ionization model in these instances.

Then, a nuclear reaction probability ($P_{LAE}$) is calculated based on the LAE model and compared to the sampled nuclear reaction probability ($sP_{LAE}$) at decision block 220. If a nuclear reaction happened (i.e., $sP_{LAE}<P_{LAE}$), a calculation is performed based on the LAE model data at step 222 and the status of the virtual particles are updated at step 224 based on the LAE model; otherwise, the virtual particles are updated at step 224 based on the CSDA model (from step 214) and/or ionization formula (from step 218). As a non-limiting example, updating the status of a virtual particle can include updating the phase space of the virtual particle (i.e., updating the momentum, energy, and/or position(s) of the virtual particle). The range shifter simulation stage ends when the virtual particles exit the range shifter, as determined at decision block 226; otherwise, if the virtual particles have not exited the range shifter the range shifter simulation block 210 is repeated. Thus, depending on the calculated ionization probability ($P_{ion}$) and nuclear reaction probability ($P_{LAE}$), the phase space of the virtual particle is updated at step 224 based on the phase space calculated using the LAE model (e.g., when $SP_{LAE}<P_{LAE}$), using the ionization model (e.g., when $sP_{ion}<P_{ion}$), and/or using the CSDA model.

The calculation in the patient geometry simulation block 212 is similar to the calculation in the range shifter simulation block 210 with some minor differences. For instance, a calculation based on the CSDA model data corresponding to the patient geometry is first performed at step 228. In some implementations, the CT DICOM coordinate can be used instead of the beam eye view coordinate. Additionally, dose scoring can be done to each voxel, which can be globally shared among all threads in memory buffers, in the patient geometry, while in some implementations no dose scoring is done in the calculation in the range shifter simulation block 210.

In the patient geometry, by comparing the ionization probability ($P_{ion}$) calculated based on the virtual particle parameters and the sampled ionization probability ($sP_{ion}$) at decision block 230, the ionization process can be considered based on an analytical formula (e.g., similar to analytical formulae used in MCsquare or other suitable MC codes) when $sP_{ion}$ is less than $P_{ion}$, as indicated at step 232. As a non-limiting example, the phase space of the virtual particle can be updated based on the ionization model in these instances.

Then, a nuclear reaction probability ($P_{LAE}$) is calculated based on the LAE model and compared to the sampled nuclear reaction probability ($sP_{LAE}$) at decision block 234. If a nuclear reaction happened (i.e., $sP_{LAE}<P_{LAE}$), a calculation is performed based on the LAE model data at step 236 and the status of the virtual particles are updated at step 238 based on the LAE model; otherwise, the virtual particles are updated at step 238 based on the CSDA model (from step 228) and/or ionization formula (from step 232). The patient geometry simulation stage ends when the virtual particles are absorbed in the patient geometry or exit the patient geometry, as determined at decision block 240; otherwise, if the virtual particles have not been absorbed or have not exited the patient geometry, range shifter the patient geometry simulation block 212 is repeated. Thus, depending on the calculated ionization probability ($P_{ion}$) and nuclear reaction probability ($P_{LAE}$), the phase space of the virtual particle is updated at step 238 based on the phase space calculated using the LAE model (e.g., when $sP_{LAE}<P_{LAE}$), using the ionization model (e.g., when $sP_{ion}<P_{ion}$), and/or using the CSDA model. The whole simulation ends when the calculation in the patient geometry ends.

The dose scoring to each voxel from each virtual particle simulated by a certain thread takes place once the virtual particle status is updated at step 238. As a non-limiting example, an atomic addition function can be used to provide for "thread-safe" operations; that is, where operations of the per-voxel dose, which can be globally shared among all threads in memory buffers, by one thread are not interfered by other threads. This can avoid possible racing conditions. The avoidance of simulating secondary particles further minimizes the chance of possible racing conditions.

Additional methods and techniques can be used to further accelerate the calculation speed and improve the calculation accuracy of the VPMC dose calculation engine. As one example, the CT resampling of a fixed resolution can be enhanced by introducing a more advanced adaptive resolution resampling method to reduce the number of the voxels, thereby accelerating the calculation speed. As another example, a bias sampling method can be used in particle generation, in which a central high-dose region of a beamlet is down-sampled while the lateral low-dose region of a beamlet is up-sampled to reduce the total number of particles for simulation. Using this technique, calculation speed can be accelerated without compromising the calculation accuracy. As yet another example, particle splitting can be used to speed up calculations, in which fewer numbers of particles are initially generated, but more particles are dynamically generated in regions with high statistical noise. In this way, the total number of particles can be reduced without compromising the calculation efficiency, thereby leading to faster calculation. Additionally or alternatively, a dynamic step size method, such as random-hinge can be used to enhance calculation efficiency.

The present disclosure thus provides for a GPU-accelerated fast MC dose calculation engine, which is based on the concept of using virtual particles to avoid the simulation of the secondary particles generated during nuclear reactions. Pre-calculated PDF databases of the relevant physics parameters are generated using a separate MC dose calculation engine, such as the MCsquare dose calculation engine. The PDFs can be stored as CUDA texture LUTs for efficient calculation in the VMPC dose calculation engine. The disclosed VPMC dose calculation engine significantly reduces the dose calculation time of a plan (e.g., reducing the dose calculation time down to 2.82±2.57 seconds, which is about 37 times faster than the typical dose calculation times using an enhanced version of MCsquare, which itself is about 5-10 times faster than the original MCsquare).

Pre-calculated parameter databases are used to increase the calculation efficiency in MC simulations by using database querying instead of on-the-fly calculation. Such techniques can perform even better on GPUs than CPUs, since the possible interpolation can be done efficiently using the unique characteristics of the GPU textures. The pre-calculated parameter databases can be updated when a charged particle therapy system is updated with a new CT calibration curve.

Compared to other CPU-based fast MC codes using pre-calculated databases, the VPMC dose calculation engine described in the present disclosure has some unique features. In Macro MC (MMC), the pre-calculated databases were generated based on macro blocks (such as slab, cylinder, or sphere). And realistic particles, including both primary and secondary particles, were simulated in the conventional way. In the track-repeating algorithm, a database of proton trajectories, including secondary protons, was generated in water with discrete steps, where the step length, angles relative to the previous step, energy loss, and energy deposit were stored. Then the extrapolation from water to other materials was achieved by scaling the path length of each step and the angle between steps. When a tracked history was selected for a proton, the proton was then transported as if it followed this assigned track. By re-tracing the proton track from the database of the pre-calculated-histories, dose distribution could be calculated in heterogeneous mediums.

The VPMC dose calculation engine uses small steps between two events (e.g., those used in conventional MC simulations) instead of macro blocks (such as slab, cylinder, or sphere) used in other CPU-based MC dose calculation engines, such as in Macro MC ("MMC"). In addition, the VPMC dose calculation engine is specifically developed for GPU-acceleration and implements a GPU-friendly concept of virtual particles to avoid the simulation of the secondary particles generated during the nuclear reaction, while MMC was originally developed for CPU-based computing platforms with conventional methods to handle secondary particles. As noted above, adapting CPU-based dose calculation engines such as MMC for use in a GPU-based computing platform would not resolve the thread divergence problem.

As described above, VPMC uses the concept of virtual particles to avoid the simulation of secondary particles generated in nuclear reactions in order to take full advantage of the computing capacity of GPUs. The concept of virtual particles also minimized or otherwise removes the chance of thread divergence in GPU threads. Each virtual particle can be simulated equivalently with the same control logic and the same memory buffer, which is advantageous for use with GPU hardware architecture. Therefore, by assigning the simulation of a virtual particle to a GPU thread, every thread within a warp can be equally executing the same computation task.

The concept of the virtual particles can be developed from the perspective of statistics, rather than the perspective of physics models. Therefore, a descriptive LAE model was used to describe the nuclear reaction, where secondary particles could be generated, with five parameters of each virtual particle: nuclear reaction probability, reflected angle, energy loss, energy deposit, and weight gain. As described above, weight gain can be an arbitrary parameter specifically introduced to get the correct final dose during the scoring stage. The PDF databases of those parameters can be pre-calculated and stored using the CUDA texture LUTs for efficient calculation. MC dose calculation codes, such as the fast CPU-based MC code, MCsquare, can be used for generating these databases by the statistical analysis of the pre-calculated primary particles in all materials defined during the commissioning of MCsquare based on selected charged particle therapy systems.

Figure 3:
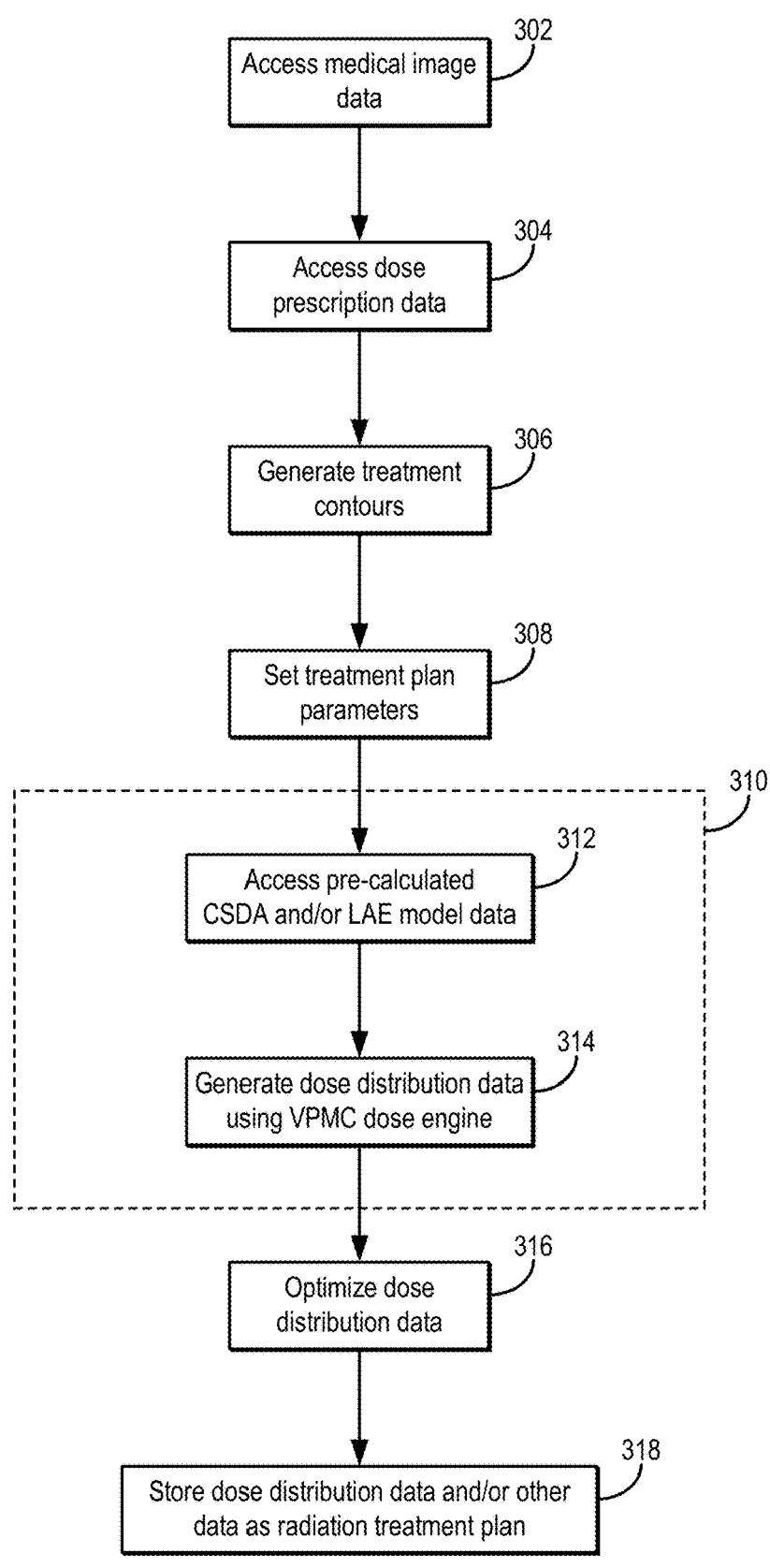
FIG. 3 is a flowchart setting forth the steps of an example method for generating a radiation treatment plan for a charged particle therapy system using a VPMC dose calculation engine to generate the dose distribution data used in the radiation treatment plan.

Referring now to FIG. 3, a flowchart is illustrated as setting forth the steps of an example method for generating a radiation treatment plan for use with a charged particle therapy system, such as a proton therapy system or heavy ion therapy system.

The method includes accessing medical image data with a computer system, as indicated at step 302. Accessing the medical image data can include retrieving previously acquired medical image data from a memory or other data storage device or medium. Additionally or alternatively, accessing the medical image data can include acquiring the medical image data with a suitable medical imaging system.

As one example, the medical image data can include medical images of a patient, which may include images acquired with a CT system.

Dose prescription data are also accessed with the computer system, as indicated at step 304. Accessing the dose prescription data can include retrieving previously generated dose prescription data from a memory or other data storage device or medium. Additionally or alternatively, accessing the dose prescription data can include generating the data with the computer system. As one example, the dose prescription data can include the prescribed dose(s) for treating one or more regions in the patient.

Treatment contour data are generated based on the medical image data and the dose prescription data, as indicated at step 306. In general, the treatment contour data include contours of treatment target volumes, organs-at-risk, and the like. The treatment contour data can also indicate the planned dose prescription to be achieved in each contoured region. Plan parameters are then set using the computer system, as indicated at step 308. Examples of plan parameters that can be set include the beam arrangement(s) to be used during treatment, the number of treatment fractions, whether pencil beam scanning should be utilized, and so on.

The dose distribution is then generated using a VPMC dose calculation engine implemented with the computer system, as indicated at process block 310. Generating the dose distribution includes accessing pre-calculated CSDA data, ionization model data, and/or LAE model data, as indicated at step 312. As described above, accessing the CSDA, ionization, and/or LAE model data can include loading the model data into shared memories of a GPU, such as by loading and storing the model data as CUDA texture LUTs. Virtual particle simulations are then performed to calculate the dose distribution based on the established plan parameters, treatment contour data, and dose prescription, as indicated at step 314. For instance, the dose simulation processes described with respect to FIG. 2 can be used.

The dose distribution stored in the dose distribution data is then optimized, as indicated at step 316. For example, the dose distribution can be optimized by inputting the dose distribution data to one or more dose optimization objective functions and optimizing the objective function(s). As is known in the art, the objective function(s) can be composed of the dose volume constraints of the tumor targets and critical organs prescribed by the treating physicians. As an example, during the optimization, the proton spot fluence map is adjusted automatically until the resulting dose distribution calculated by the VPMC dose engine meets the clinical requirements.

The optimized dose distribution data are then stored as part of the radiation treatment plan, as indicated at step 318. The medical image data, dose prescription data, treatment contour data, and/or plan parameter data can also be stored as part of the radiation treatment plan. The radiation treatment plan can be evaluated for quality assurance and updated as necessary. The final radiation treatment plan can then be provided to the control system of the charged particle therapy system to control the delivery of charged particle therapy to the patient.

Figure 4:
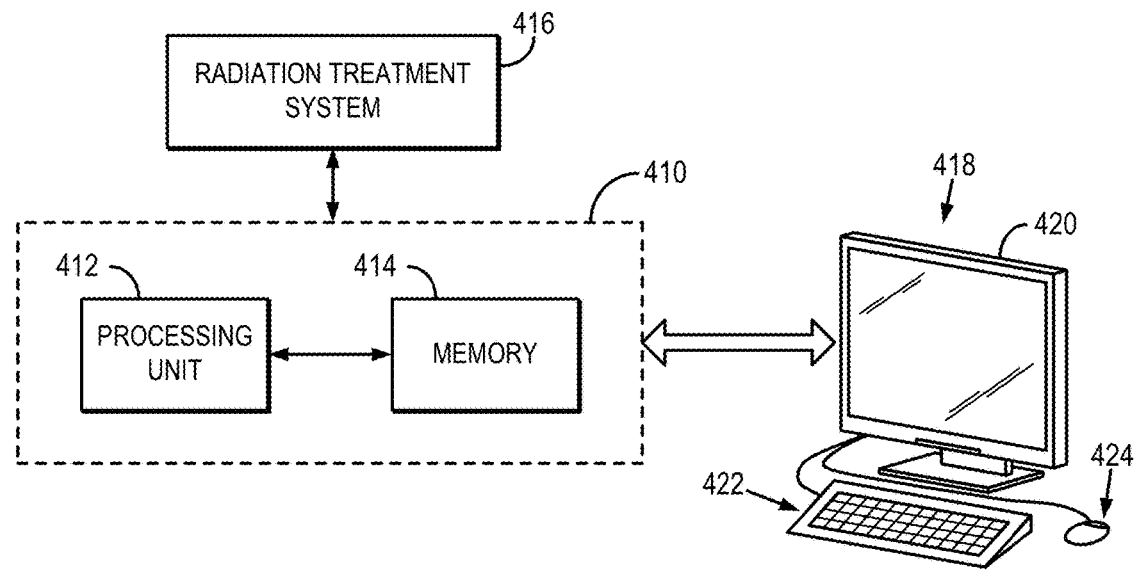
FIG. 4 is a block diagram of an example treatment planning system that can implement the methods described in the present disclosure.

As noted, the systems and methods described in the present disclosure can be implemented using a radiation treatment planning system. Referring now to FIG. 4, an example of such a radiation treatment planning system 410 is illustrated. The radiation treatment planning system 410 is preferably in communication with one or more radiation treatment systems 412, which may include any suitable radiation treatment system.

The radiation treatment planning system 410 generally includes a memory 414 that is operably coupled to a processor unit 416. As an example, the processor unit 416 can be a commercially available computer processor, such as those described above. The processor unit 416 is configured to carry out one or more of the steps of the methods described above.

As an example, the memory 414 can include a plurality of memory elements, or can include a single memory element. In general, the memory 414 is configured to store information regarding patient data, a treatment target (e.g., a tumor located within a patient), imaging beam model data, treatment beam model data, dose matrices, and so on.

Preferably, the radiation treatment planning system 410 includes, or is otherwise in communication with, a user interface 418. As an example, the user interface 418 provides information to a user, such as a medical physicist. For example, the user interface 418 can include a display 420 and one or more input devices, such as a keyboard 422 and mouse 424.

Figure 5:
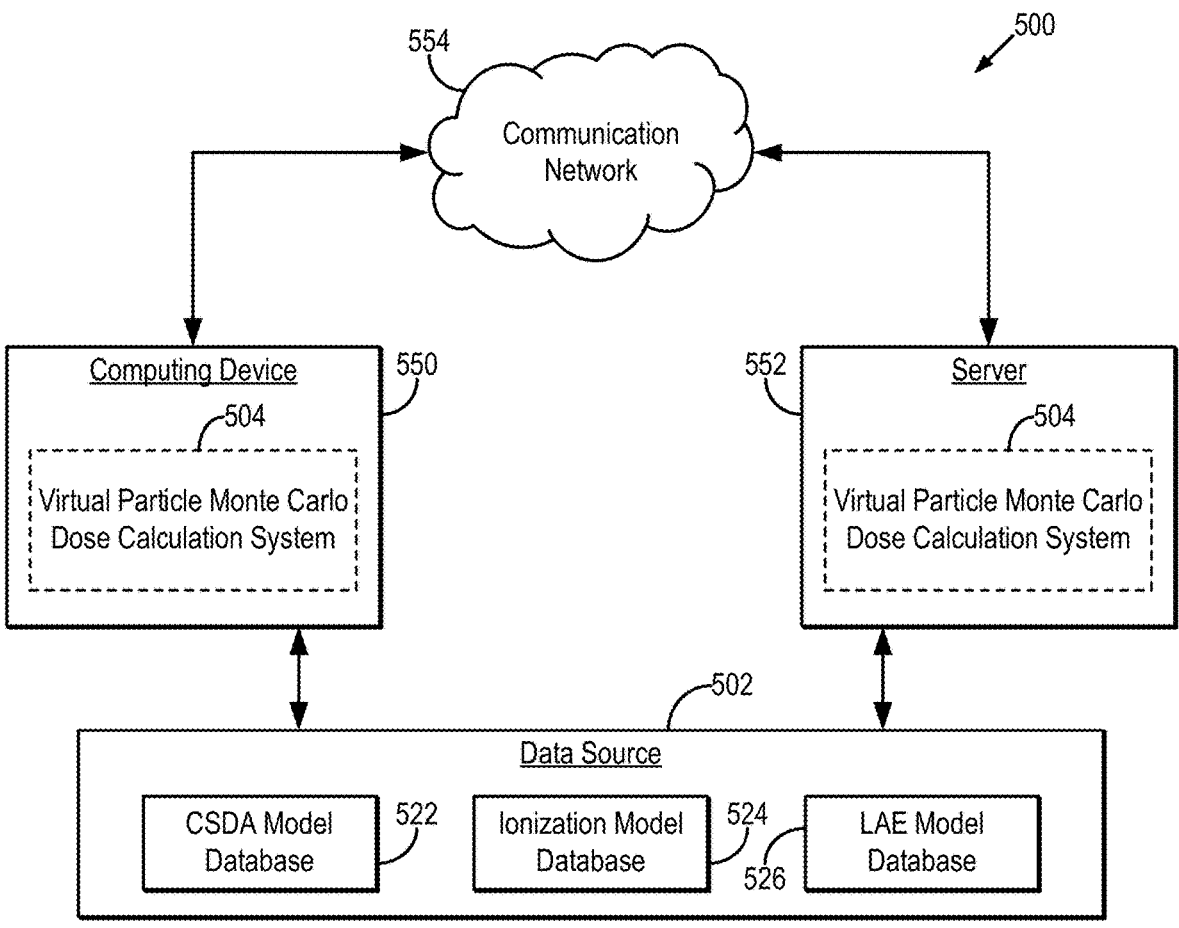
FIG. 5 is a block diagram of an example system that can implement a VPMC dose calculation engine according to some embodiments described in the present disclosure.

Referring now to FIG. 5, an example of a system 500 for virtual particle Monte Carlo ("VPMC") dose calculation in accordance with some embodiments of the systems and methods described in the present disclosure is shown. As shown in FIG. 5, a computing device 550 can receive one or more types of data (e.g., CSDA model data, ionization model data, LAE model data) from data source 502, which may include one or more CSDA model databases 522, one or more ionization model databases 524, and one or more LAE model databases 526 storing pre-calculated CSDA, ionization, and LAE model parameter data, respectively. In some embodiments, computing device 550 can execute at least a portion of a virtual particle dose calculation system 504 to generate dose distribution data based in part on data received from the data source 502 and using a virtual particle framework.

Additionally or alternatively, in some embodiments, the computing device 550 can communicate information about data received from the data source 502 to a server 552 over a communication network 554, which can execute at least a portion of the virtual particle dose calculation system 504. In such embodiments, the server 552 can return information to the computing device 550 (and/or any other suitable computing device) indicative of an output of the virtual particle dose calculation system 504.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552.

In some embodiments, data source 502 can be any suitable source of data (e.g., CSDA model data, LAE model data), such as one or more CSDA model databases 522, one or more ionization model databases 524, and/or LAE model databases 526; another computing device (e.g., a server storing CSDA model data, ionization model data, LAE model data), and so on. In some embodiments, data source 502 can be local to computing device 550. For example, data source 502 can be incorporated with computing device 550 (e.g., computing device 550 can be configured to include one or more databases for storing pre-calculated CSDA model data, ionization model data, LAE model data, or the like). As another example, data source 502 can be connected to computing device 550 by a cable, a direct wireless link, and so on. Additionally or alternatively, in some embodiments, data source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), other types of wireless network, a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
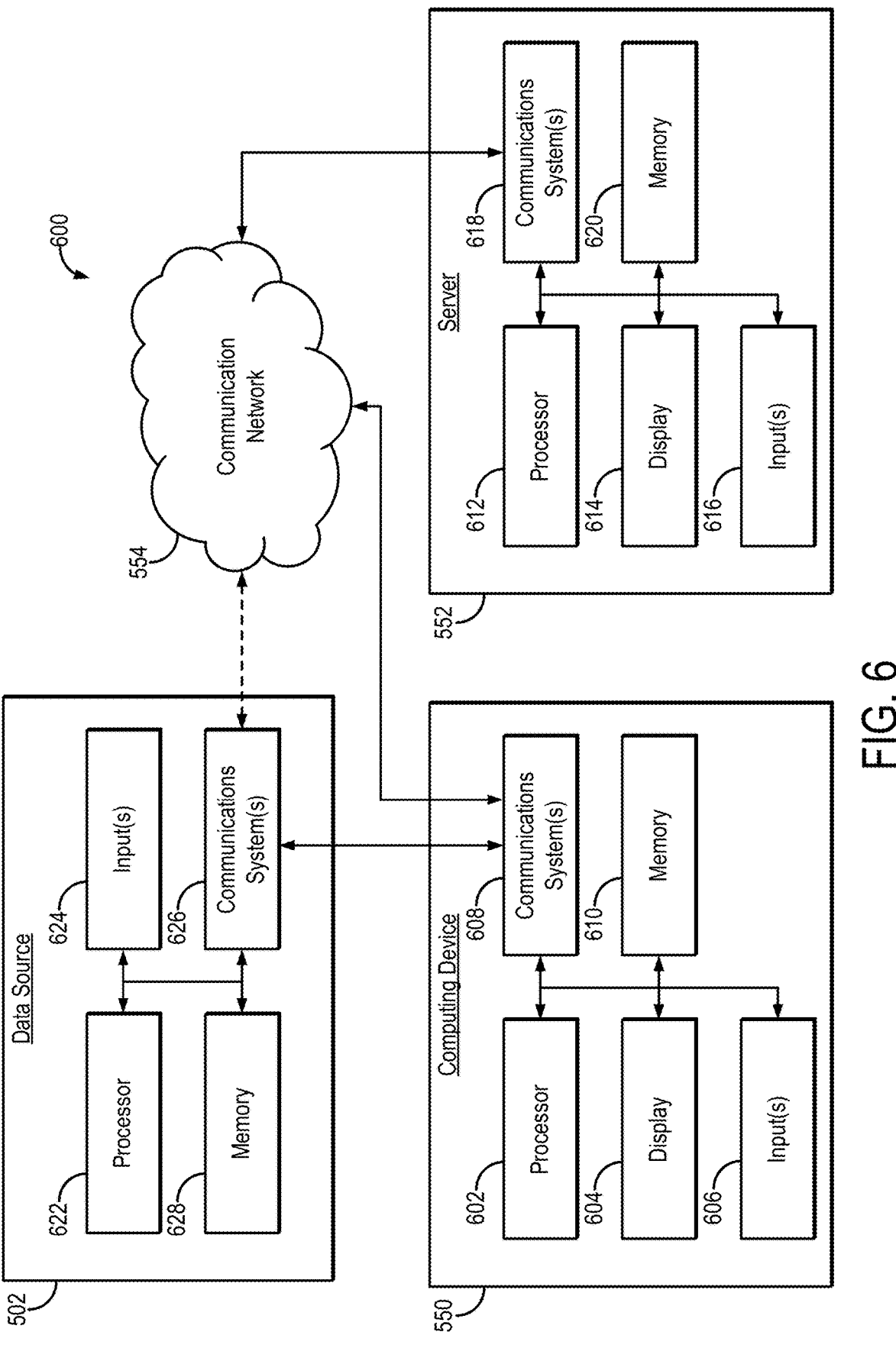
FIG. 6 is a block diagram of example components that can implement the system of FIG. 5.

Referring now to FIG. 6, an example of hardware 600 that can be used to implement data source 502, computing device 550, and server 552 in accordance with some embodiments of the systems and methods described in the present disclosure is shown.

As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. As noted above, in a preferred embodiment the processor 602 of the computing device 550 includes one or more GPUs for implementing the VPMC dose calculation engine. Each GPU can have on-board shared GPU memories for storing data as described in the present disclosure. In some embodiments, the computing device 550 may also include one or more CPUs for performing functions other than implementing the VPMC dose calculation engine.

In some embodiments, display 604 can include any suitable display devices, such as a liquid crystal display ("LCD") screen, a light-emitting diode ("LED") display, an organic LED ("OLED") display, an electrophoretic display (e.g., an "e-ink" display), a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware, and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display

604, to communicate with server 552 via communications system(s) 608, and so on. Memory 610 can include any suitable volatile memory, non-volatile memory, storage, or any suitable combination thereof. For example, memory 610 can include random-access memory ("RAM"), read-only memory ("ROM"), electrically programmable ROM ("EPROM"), electrically erasable ROM ("EEPROM"), other forms of volatile memory, other forms of non-volatile memory, one or more forms of semi-volatile memory, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on. For example, the processor 602 and the memory 610 can be configured to perform the methods described herein (e.g., the method of FIG. 2, the method of FIG. 3).

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as an LCD screen, LED display, OLED display, electrophoretic display, a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware, and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, the server 552 is configured to perform the methods described in the present disclosure. For example, the processor 612 and memory 620 can be configured to perform the methods described herein (e.g., the method of FIG. 2, the method of FIG. 3).

In some embodiments, data source 502 can include a processor 622, one or more inputs 624, one or more communications systems 626, and/or memory 628. In some embodiments, processor 622 can be any suitable hardware processor or combination of processors, such as a CPU, a GPU, and so on. In some embodiments, the one or more input 624 are generally configured to receive data, instructions, user input, or the like. Additionally or alternatively, in some embodiments, the one or more inputs 624 can include any suitable hardware, firmware, and/or software for coupling to and/or controlling operations of the data source 502. In some embodiments, one or more portions of the inputs 624 can be removable and/or replaceable.

Note that, although not shown, data source 502 can include any suitable inputs and/or outputs. For example, data source 502 can include input devices and/or sensors that can be used to receive user input, such as a keyboard, a mouse, a touchscreen, a microphone, a trackpad, a trackball, and so on. As another example, data source 502 can include any suitable display devices, such as an LCD screen, an LED display, an OLED display, an electrophoretic display, a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware, and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more data acquisition systems 624, and/or receive data from the one or more data acquisition systems 624; to generate images from data; present content (e.g., data, images, a user interface) using a display; communicate with one or more computing devices 550; and so on. Memory 628 can include any suitable volatile memory, non-volatile memory, storage, or any suitable combination thereof. For example, memory 628 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 628 can have encoded thereon, or otherwise stored therein, a program for controlling operation of data source 502. In such embodiments, processor 622 can execute at least a portion of the program to generate images, transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer-readable media can be used for storing instructions for performing the functions and/or processes described herein. For example, in some embodiments, computer-readable media can be transitory or non-transitory. For example, non-transitory computer-readable media can include media such as magnetic media (e.g., hard disks, floppy disks), optical media (e.g., compact discs, digital video discs, Blu-ray discs), semiconductor media (e.g., RAM, flash memory, EPROM, EEPROM), any suitable media that is not fleeting or devoid of any semblance of permanence during transmission, and/ or any suitable tangible media. As another example, transitory computer-readable media can include signals on networks, in wires, conductors, optical fibers, circuits, or any suitable media that is fleeting and devoid of any semblance of permanence during transmission, and/or any suitable intangible media.

As used herein in the context of computer implementation, unless otherwise specified or limited, the terms "component," "system," "module," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

The present disclosure has described one or more preferred embodiments, and it should be appreciated that many equivalents, alternatives, variations, and modifications, aside from those expressly stated, are possible and within the scope of the invention.

The invention claimed is:

1. A treatment planning system for use with a charged particle therapy system, comprising:
   a memory having stored thereon:
      a pre-calculated continuous-slowing-down-approximation (CSDA) model comprising probability distribution functions (PDFs) of physics parameters associated with soft particle interactions of virtual particles;

a pre-calculated ionization model comprising PDFs of physics parameters associated with ionization of virtual particles; and
   a pre-calculated large angle scattering event (LAE) model comprising PDFs of physics parameters associated with hard particle interactions of virtual particles;
   a graphics processing unit (GPU) configured to:
      load the CSDA model, the ionization model, and the LAE model into a shared memory of the GPU;
      simulate virtual particles using the CSDA model, the ionization model, and the LAE model, wherein the virtual particles are simulated by simulating both primary charged particles and secondary particles as virtual particles that start at a same starting location of a primary charged particle; and
      calculate a dose distribution of the primary charged particles and the secondary particles based on the simulated virtual particles;
   wherein the GPU is configured to simulate virtual particles by:
      assigning each virtual particle to a thread of the GPU thereby minimizing thread divergence and racing conditions in the GPU; and
      in each of a plurality of steps:
         calculating a phase space for each virtual particle based on at least one of the CSDA model, the ionization model, or the LAE model; and
         updating each virtual particle based on the calculated phase space.

2. The treatment planning system of claim 1, wherein the GPU is configured to load the CSDA model, the ionization model, and the LAE model into the shared memory of the GPU by storing the CSDA model, the ionization model, and the LAE model as compute unified device architecture (CUDA) textures look-up tables in the shared memory.

3. The treatment planning system of claim 1, wherein the GPU is configured to calculate the phase space for each virtual particle by calculating an updated phase space of each virtual particle based on at least one of the CSDA model, the ionization model, or the LAE model.

4. The treatment planning system of claim 1, wherein the GPU is configured to, for each virtual particle in each of the plurality of steps:
   calculate the phase space for the virtual particle based on the ionization model;
   compare an ionization probability calculated for the virtual particle with a sampled ionization probability;
   if the calculated ionization probability is less than the sampled ionization probability, update the phase space of the virtual particle based on the phase space calculated based on the ionization model.

5. The treatment planning system of claim 1, wherein the GPU is configured to, for each virtual particle in each of the plurality of steps:
   calculate the phase space for the virtual particle based on the LAE model;
   compare a nuclear reaction probability calculated for the virtual particle with a sampled nuclear reaction probability;
   if the calculated nuclear reaction probability is less than the sampled nuclear reaction probability, update the phase space of the virtual particle using the phase space calculated based on the LAE model.

6. The treatment planning system of claim 1, wherein the GPU is configured to calculate the dose distribution by, during a dose scoring stage, multiplying a weight gain value to a dose contribution of each virtual particle in each of the plurality of steps.

7. The treatment planning system of claim 6, wherein each weight gain value corresponds to a fractional share of a same path shared by multiple virtual particles in each of the plurality of steps.

8. The treatment planning system of claim 1, wherein the GPU is configured to simulate the virtual particles in a range shifter and a patient geometry, such that virtual particles are simulated in the range shifter using first CSDA data in the CSDA model, first ionization data in the ionization model, and first LAE data in the LAE model and virtual particles are simulated in the patient geometry using second CSDA data in the CSDA model, second ionization data in the ionization model, and second LAE data in the LAE model.

9. The treatment planning system of claim 8, wherein the GPU is configured to load the CSDA model, the ionization model, and the LAE model into the shared memory of the GPU by storing the CSDA model, the ionization model, and the LAE model as compute unified device architecture (CUDA) textures in the shared memory.

10. The treatment planning system of claim 9, wherein the first CSDA data, the first ionization data, and the first LAE data are stored as one-dimensional CUDA textures in the shared memory, and the second CSDA data, second ionization data, and the second LAE data are stored as two-dimensional CUDA textures in the shared memory.

11. The treatment planning system of claim 1, wherein the pre-calculated CSDA model, the pre-calculated ionization model, and the pre-calculated LAE model correspond to models generated based on a statistical analysis of realistic particle track histories generated using a Monte Carlo simulation.

12. The treatment planning system of claim 1, wherein the pre-calculated ionization model comprises PDFs of physics parameters comprising deposited energy, energy straggling, deflection angle, and ionization probability.

13. The treatment planning system of claim 1, wherein the pre-calculated LAE model comprises PDFs of physics parameters comprising deposited energy, energy loss, deflection angle, and nuclear reaction probability.

14. The treatment planning system of claim 13, wherein the pre-calculated LAE model further comprises weight gain values corresponding to fractional shares of a same path shared by multiple virtual particles in each of the plurality of steps.

15. The treatment planning system of claim 1, wherein the physics parameters are parameterized in the pre-calculated CSDA model, the pre-calculated ionization model, and the pre-calculated LAE model based on an energy (E) of a virtual particle and a Hounsfield unit value (HU) of a virtual particle.

16. The treatment planning system of claim 1, wherein the GPU is configured to simulate the virtual particles by initializing each virtual particle by sampling an energy, position, and momentum for each virtual particle.

17. The treatment planning system of claim 16, wherein the GPU is configured to sample an energy, position, and momentum for each virtual particle using a single set of phase space parameters.

18. A method for generating treatment plan data for use with a charged particle therapy system, the method comprising:

(a) loading to a shared memory of a graphics processing unit (GPU):

a pre-calculated continuous-slowing-down-approximation (CSDA) model comprising probability distribution functions (PDFs) of physics parameters associated with soft particle interactions of virtual particles;

a pre-calculated ionization model comprising PDFs of physics parameters associated with ionization of virtual particles; and a pre-calculated large angle scattering event (LAE) model comprising PDFs of physics parameters associated with hard particle interactions of virtual particles;

(b) simulating virtual particles using the GPU, wherein simulating the virtual particles comprises simulating both primary charged particles and secondary particles as virtual particles that start at a same starting location of a primary charged particle by assigning each virtual particle to a thread of the GPU thereby minimizing thread divergence and racing conditions in the GPU, and in each of a plurality of steps:

calculating a phase space for each virtual particle based on at least one of the CSDA model, the ionization model, or the LAE model; and updating each virtual particle based on its calculated phase space;

(c) generating dose distribution data based on dose scoring the simulated virtual particles using a computer system; and (d) storing the dose distribution data as part of treatment plan data for use with a charged particle therapy system.

* * * * *